United States Patent [19]

Barrault et al.

[11] 4,161,493

[45] Jul. 17, 1979

[54] PROCESS FOR THE PRODUCTION OF MERCAPTANS

[75] Inventors: Joël Barrault, Liguge; Michel Guisnet, Poitiers; Jacques Lucien, Le Mesnil Esnard; Raymond Maurel, Jaunay Clan, all of France

[73] Assignee: Societe Nationale Elf Aquitaine (Production), France

[21] Appl. No.: 897,387

[22] Filed: Apr. 18, 1978

[30] Foreign Application Priority Data

Apr. 21, 1977 [FR] France .................................. 77 12002

[51] Int. Cl.$^2$ .......................................... C07C 148/00
[52] U.S. Cl. .............................. 260/609 R; 260/609 D
[58] Field of Search ............ 260/609 R, 609 D, 607 C

[56] References Cited

U.S. PATENT DOCUMENTS

| 2,051,806 | 8/1936 | Allen | 260/609 R |
| 2,402,613 | 6/1946 | Farlow et al. | 260/609 R |
| 2,402,615 | 6/1946 | Farlow et al. | 260/609 R |
| 2,402,694 | 6/1946 | Tanner | 260/609 D |
| 2,437,985 | 3/1948 | Winkler et al. | 260/607 C |
| 3,994,980 | 11/1976 | Kubicek | 260/609 D |

OTHER PUBLICATIONS

J. W. Greidanus, Canadian Journal of Chemistry, vol. 48, (1970), pp. 3531-3536, Chemistry of 2-substituted adamantanes, I, Adamantanethione, its dimer and trimer.

J. W. Greidanus, Canadian Journal of Chemistry, vol. 48, (1970), pp. 3593-3597, Chemistry of 2-substituted adamantanes, II, preparation of 2-adamantanethiol and some of its derivatives.

*Primary Examiner*—Donald G. Daus
*Assistant Examiner*—M. C. Eakin
*Attorney, Agent, or Firm*—Ostrolenk, Faber, Gerb & Soffen

[57] ABSTRACT

The invention concerns a new process for the production of primary and secondary mercaptans.

The invention is based on the fact that it is possible to cause an hydrogen exchange between a thioaldehyde or a thioketone and a mercaptan with very good selectivity and conversion yields.

15 Claims, No Drawings

PROCESS FOR THE PRODUCTION OF MERCAPTANS

The invention concerns a new process for the production of primary and secondary mercaptans.

Due to the increasing demands for mercaptans in industry and to certain drawbacks in their known preparation processes, it is desirable to develop a more satisfactory process of preparation. Among the conventional methods for synthesizing mercaptans, one of the most widely used consists in reacting hydrogen sulphide, under heating, with alcohols, in the presence of catalysts; this process gives unfavourable yields when applied to the process of obtention of secondary mercaptans since the sulfohydrolysis of alcohols entails the formation of a high proportion of olefins. The known method which consists in catalytic addition of $H_2S$ on the olefins under pressure and under heating remains limited to the use of symetric alkenes, which are the only olefins which do not lead to the formation of two isomeric thiols. As to the photochemical addition of $H_2S$ to the olefins, it gives rise to an appreciable production of sulphur, in addition to the formation of mercaptan. The action of hydrogen sulphide on aldehydes or ketones, in the presence of hydrogen, under heating and under high pressure, is also known, but this process is also unsuitable for the industrial preparation of mercaptan.

The present invention provides a process which constitutes a substantial improvement over the known processes, not only with respect to the high increase in mercaptan yields but also on account of the fact that it allows the obtention of thiols, which were difficult, if not impossible, to prepare by known methods. More particularly, the novel process renders possible the obtention, with high yields, of secondary mercaptans, one or two of the radicals of which are branched and, in previous processes, subject to dehydration and isomerization.

A particularity of this novel process is the transformation of a thiocarbonyl derivative into mercaptan having the same skeleton, under the action of another available mercaptan or the transformation of a carbonyl derivative under the double action of hydrogen sulphide and an available mercaptan.

The invention is based on the fact that it is possible to cause the hydrogen exchange between a thio-aldehyde or a thio-ketone, on the one hand, and a mercaptan on the other hand, with very good selectivity and conversion yields, under conditions which are easily adaptable to production on an industrial scale.

An object of the present invention is a process wherein a thio-aldehyde or a thio-ketone is heated in the presence of a metallic oxide catalyst so as to cause the hydrogen exchange between this thio-aldehyde, or thio-ketone, and the mercaptan.

The reaction which takes place, according to the invention, can be illustrated as follows:

(1) using a thio-aldehyde as raw material

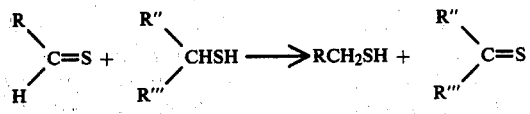

(2) using a thio-ketone as raw material

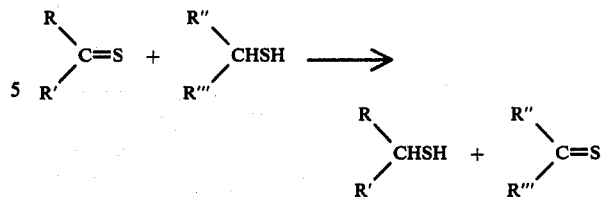

Thus it is noted that the invention allows the obtention of a primary $RCH_2SH$ thiol from the corresponding thio-aldehyde by treating the latter with another primary or secondary thiol which provides it with the necessary hydrogens. In the same way, a secondary $RR'CHSH$ thiol is obtained from the corresponding $RR'C=S$ thio-ketone by treating this thio-ketone with another available primary or secondary thiol.

The process according to the invention can be carried out at temperatures in the range of 100° to 300° C. and more particularly between 150° and 300° C., depending on the nature of the mercaptan to be obtained; the preparation necessitates the presence of a catalyst, usually constituted by one or several oxides of the metals from groups II and III of the Periodic Table, especially alumina or magnesia, preferably activated by an alkaline base.

According to one important feature of the invention, the thio-aldehyde or thio-ketone can be produced in situ, at the same time as the hydrogen exchanges, from the corresponding aldehyde or ketone. Since this aldehyde or ketone are much more easily available in industry than their thio-analogues, this manner of performing the novel process is of very great interest.

According to this embodiment of the invention, the aldehyde or ketone is reacted with $H_2S$ to transform them respectively into thio-aldehyde or thio-ketone, simultaneously with the exchange of hydrogen. Thus this exchange according to the reaction (1) or (2) occurs at the same time as the transformation of the aldehyde or the ketone into the corresponding thio-derivative. The global process of the invention can thus be represented as follows:

(3) from an aldehyde as raw product:

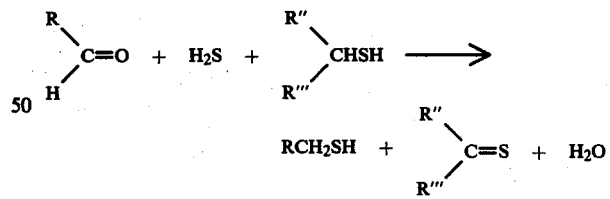

(4) from a ketone as raw product:

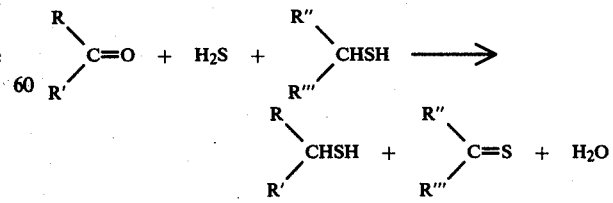

In other words, in accordance with the invention, the required primary $RCH_2SH$ or secondary $RR'CHSH$ mercaptan can be obtained by reacting a carbonyl compound, R or R and R' radical carrier, with hydrogen sulphide, at the same time as with an ordinary available primary R"CH₂SH or secondary R"R'"CHS mercaptan.

The radicals R, R', R", R'", similar or different, can be alkyls particularly $C_1$ to $C_{18}$ alkyls, cycloalkyls or aryls, especially phenyls or alkyl-phenyls. R can form a cycle with R' and possibly with R" and R'". Moreover one or more of the symbols R to R'" can designate hydrogen atoms.

For example, [equation (3)], the RCHO aldehydes can be formaldehyde, acetaldehyde, propionaldehyde, butyraldehyde, heptanal, octanal, dodecanal, octadecanal, furfural, benzaldehyde, toluylaldehyde, anisaldehyde, etc.

Among the numerous ketones which can be used, the following may be cited by way of example: diethylketone, ethyl-methyl-ketone, methyl-hexyl-ketone (2-octanone), methyl-n.octyl-ketone, (2-decanone), propyl-n.hexyl-ketone (4-decanone), propyl-isobutyl-ketone, methyl-ter.butyl-ketone, cyclopentanone, cyclohexanone, cycloheptanone, benzophenone, acetophenone, propiophenone, amyl-phenyl-ketone, ditolylketone, etc.

Any ordinary mercaptans, primary or secondary, aliphatic, cycloaliphatic or arylic may be used as a thiol for the hydrogen exchange, that is to say as the thiol "partner." Thus with methyl-mercaptan, which is easily available and inexpensive, it becomes possible to obtain extremely varied thiols wherein R and/or R' are more or less heavy radicals, possibly branched, which were difficult to obtain by the known methods. In order to facilitate the separation of the desired product, the thiol partner must be carefully chosen; it must have a boiling point as different as possible from that of the mercaptan to be prepared.

The alumina, known under the designation of alumina "A," is a very appropriate catalyst, the performances of which can be further improved by the addition of basic substances, particularly alkaline oxides and more especially KOH. The best results are obtained with alumina containing 2 to 10% of $K_2O$. Magnesium oxide, although less active than alumina, gives nevertheless good results too. Other oxides of the metals from groups II and III of the Periodic Table can be used alone or mixed with each other.

The necessary contact time between the gaseous reaction mixture and the catalyst varies with the temperature, the nature of the reaction medium and the catalyst, but it is usually in the range of 1 to 16 seconds; this contact time is however not critical and it can be prolonged depending on the reactivity of the carbonyl compound used.

According to the equations (3) and (4), one $H_2S$ mole alone and one thiol partner are required to transform the carbonyl compound. However, since the reactions concerned are balanced, it is preferable to operate with an excess of each of the reagents. The best results are obtained with a molar ratio: $a = H_2S/$carbonyl compound $\geq 5$ and $b = $thiol partner/carbonyl compound $\geq 3$.

It should be noted that the excess thiol partner can be recycled as easily as the hydrogen sulphide.

The reaction, according to the invention, takes place in a gaseous phase at atmospheric pressure, but it may also occur under higher pressure.

The invention is described in the following examples but is not confined thereto.

In Examples 1 to 15, the preparation of 3,3-dimethyl-butane-2-thiol from pinacolone, $H_2S$ and methyl-mercaptan is described. The reason why this particular preparation was chosen in order to illustrate the invention is that selective obtention of this branched alkyl thiol is particularly difficult to achieve with other methods, due to very easy dehydration and isomerization of the 3-3-dimethyl-butyl skeleton.

The global reaction is:

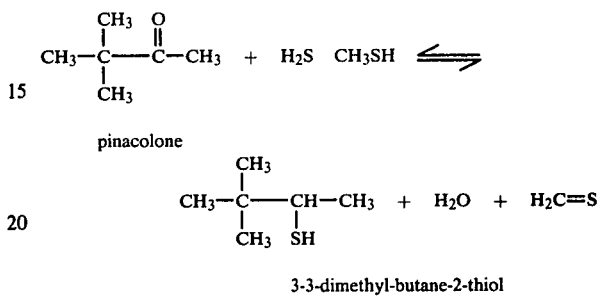

3-3-dimethyl-butane-2-thiol

In fact, the reaction here-above produces intermediary substances in small quantities, particularly thiopinacolone and secondary substances such as 3-3-dimethyl-1-butene, 3-3-dimethyl-2-butanol, formaldehyde and methanol.

EXAMPLES 1 TO 6

The aim of these examples is to illustrate the influence of the molar ratio $a = H_2S/$pinacolone on the formation of thiol. The catalyst is alumina A impregnated with 4% $K_2O$. The reaction is performed at 250° C., with a contact time of 1.2 seconds and a molar ratio $b = CH_3SH/$pinacolone which is constant and equal to 5. In the Table 1 hereinafter, for every value of ratio a, the global activity of the catalyst expressed in moles $h^{-1}kg^{-1}$ (number of pinacolone moles transformed per hour and per kg of catalyst) are given, as well as the various selectivity rates of the formed products after the reaction has been functioning for 20 hours.

It will be noted that a large excess of hydrogen sulphide enables the activity of the catalyst to be increased. Moreover a good stability of the catalytic system was observed in all cases.

TABLE 1

| Ex | a | Global activity (mole⁺¹h⁻¹kg⁻¹) | Selectivity (%) for thiol | olefin | thione | alcohol |
|---|---|---|---|---|---|---|
| 1 | 30 | 3.8 | 91.3 | 3.5 | 5.1 | ε |
| 2 | 20 | 3.3 | 93.4 | 2.6 | 3.9 | ε |
| 3 | 10 | 2.3 | 94.6 | 2.4 | 3.0 | ε |
| 4 | 5 | 1.8 | 95.6 | 2.1 | 2.3 | ε |
| 5 | 3 | 1.1 | 97.5 | 1.1 | 1.4 | ε |
| 6 | 1 | 0.5 | 98.0 | 1.0 | 1.0 | ε |

EXAMPLES 7 TO 10

Influence of molar ratio $b = CH_3SH/$pinacolone on the formation of thiol, the other operating conditions being the same as those of Examples 1 to 6, for a ratio $a = H_2S/$pinacolone$= 20$. The results in Table 2 were obtained after the catalyst had been functioning for 12 hours.

TABLE 2

| Ex | b | Global activity (mole$^{+1}$h$^{-1}$kg$^{-1}$) | Selectivity (%) for | | | |
|---|---|---|---|---|---|---|
| | | | thiol | olefin | thione | alcohol |
| 7 | 10 | 3.8 | 92.8 | 3.0 | 3.6 | 0.6 |
| 8 | 5 | 3.7 | 90.6 | 4.1 | 4.7 | 0.6 |
| 9 | 3 | 3.7 | 84.8 | 5.8 | 8.7 | 0.7 |
| 10 | 1 | 3.5 | 76.6 | 7.1 | 15.6 | 0.7 |

These results show that the use of a large excess of a thiol partner does not influence the activity of the catalyst. However, in order to obtain good stability of the catalytic system and good thiol selectivity rates, it is preferable to work with ratios $b \geq 3$.

EXAMPLES 11 TO 14

Influence of temperature.

The preparation of 3,3-dimethyl-butane-2-thiol was carried out using the same catalytic system (Al$_2$O$_3$+4%K$_2$O) with the molar ratios a and b equal to 5, the contact time being 1.2 seconds. Table 3 gives the results obtained after 20 hours of functioning.

TABLE 1

| Ex | T °C. | Global activity (Mole $^{+1}$h$^{-1}$kg$^{-1}$) | Selectivity (%) for | | | |
|---|---|---|---|---|---|---|
| | | | thiol | olefin | thione | alcohol |
| 11 | 170 | 0.8 | ~100 | ε | ε | ε |
| 12 | 200 | 1.1 | 99.6 | | 0.3 | ε |
| 13 | 250 | 1.8 | 95.6 | 2.1 | 2.3 | ε |
| 14 | 330 | 2.0 | 82.0 | 12.1 | 5.8 | 0.1 |

It will be noted that the elevation in temperature has neither a marked influence on the activity of the catalyst nor on the production of mercaptan: above 300° C., the formation of olefins is favored to the detriment of thiol. Due to this fact the synthesis is preferably carried out at temperatures comprised between 100° and 300° C.

EXAMPLES 15 TO 17

Influence of contact time.

Tests of formation of 3,3-dimethyl-butane-2-thiol were performed at 250° using an Al$_2$O$_3$+4%K$_2$O catalyst with molar ratios a and b equal to 5. The influence of the contact time on the pinacolone conversion and on the thiol selectivity was studied.

Table 4

| Ex | δ(s) | Conversion (%) of the pinacolone | Selectivity (%) for | | | |
|---|---|---|---|---|---|---|
| | | | thiol | olefin | thione | alcohol |
| 15 | 1.7 | 39.2 | 95.2 | 1.5 | 1.8 | 1.5 |
| 16 | 3.9 | 59.0 | 92.4 | 3.4 | 2.5 | 1.7 |
| 17 | 7.8 | 73.6 | 90.3 | 4.8 | 3.1 | 1.8 |

These results obtained after 20 hours of functioning show that even with a high pinacolone conversion rate the 3-3-dimethyl-butane-2-thiol selectivity remains high.

EXAMPLES 18 TO 24

Influence of the nature of the catalyst.

Different catalysts were tested at 250° C., with molar ratios a and b equal to 5, and with a contact time of 3.9 seconds for the same synthesis of 3-3-dimethyl-butane-2-thiol. The tested catalysts were constituted by a basic component fixed on an alumina support either by impregnation (K$_2$O) or by simply mixing (MgO).

The activity and selectivity rates after 20 hours of functioning are listed in Table 5.

It is noted that the addition of magnesium oxide to the alumina can improve the thiol selectivity, but does not seem to influence the global activity of the catalyst. On the other hand, an impregnation with KOH not only improves the activity but also the thiol selectivity. The study of a series of KOH-alumina catalysts show that there exists an optimum for the formation of thiol; this optimum is between 4 and 10% of K$_2$O.

Table 5

| Ex | Catalyst | Global Activity (mole$^{+1}$h$^{-1}$kg$^{-1}$) | Selectivity (%) for | | | |
|---|---|---|---|---|---|---|
| | | | thiol | olefin | thione | alcohol |
| 18 | Al$_2$O$_3$ | 0.72 | 74.5 | 6.3 | 18.3 | 0.8 |
| 19 | Al$_2$O$_3$+1.5%K$_2$O | 1.38 | 87.7 | 1.3 | 9.0 | 2.0 |
| 20 | Al$_2$O$_3$+4%K$_2$O | 2.71 | 92.4 | 3.4 | 2.5 | 1.7 |
| 21 | Al$_2$O$_3$+10.5%K$_2$O | 1.45 | 95.5 | 2.2 | 2.0 | 0.3 |
| 22 | Al$_2$O$_3$—MgO (50-50) | 0.73 | 86.2 | 3.1 | 8.8 | 1.9 |
| 23 | Al$_2$O$_3$—MgO (10-90) | 0.58 | 94.4 | 2.0 | 0.8 | 2.7 |
| 24 | MgO | 0.37 | 88.0 | 2.2 | ε | 9.7 |

EXAMPLES 25 TO 28

Using other ketones; comparison with pinacolone.

These examples allow the respective reactivity rates of the various ketones to be compared under the following operating conditions: catalyst Al$_2$O$_3$+4.4%K$_2$O; T=200° C.; a=b=5; δ=15.8s Table 6

| Ex | Ketone | Ketone convertion (%) | Selectivity (%) for | | | |
|---|---|---|---|---|---|---|
| | | | thiol | olefin | thione | alcohol |
| 25 | Pinacolone | 71.5 | 90.9 | 2.8 | 3.1 | 3.2 |
| 26 | Butanone | 74.0 | 91.2 | 1.6 | 5.4 | 1.8 |
| 27 | Cyclopentanone | 95.0 | 96.5 | 1.0 | 0.3 | 2.2 |
| 28 | Cyclohexanone | 95.5 | 97.0 | 1.0 | 0.5 | 1.5 |

The process according to the invention can thus be applied to various ketones and the thiol yields are always high. Example 28 shows the advantage of this new method of preparing cyclohexanethiol, the yield obtained when the latter is prepared from cyclohexanol usually being much lower.

EXAMPLES 29 TO 31

Preparation of primary thiols from aldehydes.

These examples allow the activity of the aldehydes to be compared to that of the pinacolone, under the following conditions: catalyst Al$_2$O$_3$+4.4%K$_2$O; T=250° C.; a=10; δ=9.3s. It should be noted that in the present synthesis for the obtention of primary thiols from aldehydes, it is necessary to operate at a higher temperature, in order to prevent, or at least reduce, the formation of heavy compounds.

Table 7

| Ex | Carbonyl compound | Carbonyl compound Conversion (%) | Selectivity (%) for | | | | |
|---|---|---|---|---|---|---|---|
| | | | thiol | olefin | thicarbonyl | alcohol | other components |
| 29 | Pinacolone | 93.5 | 76.0 | 15.0 | 5.0 | 4.0 | |
| 30 | Isobutyral aldehyde | 98.2 | 96.0 | 2.3 | 0.2 | 1.5 | |
| 31 | Heptanal | 99.8 | 81.5 | 4.5 | 0.9 | 1.1 | 12.0 |

Thus the invention applies to ketones as well as to aldehydes, since the conversion rate of the reagents are very high under these operating conditions. Moreover the selectivity for synthesized primary thiols is remarkable and the catalyst is very stable.

EXAMPLES 32 TO 34

Influence of the nature of the thiol partner.

The methyl-mercaptan, used in the previous examples as the thiol partner, has the advantage of being less costly than its higher homologues. Nevertheless, the preparation of 3,3-dimethyl-3-butane-2-thiol was also preformed using isopropyl mercaptan and lauryl mercaptan. The operating conditions are the following: a=10; b=5; δ=5.4s.; T=280° C. The results in Table 8 are given after the catalyst (Al$_2$O$_3$+4%K$_2$O) has functioned for 10 hours.

Table 8

| Ex | Thiol partner | pinacolone conversion | Selectivity (%) for | | | |
|---|---|---|---|---|---|---|
| | | | thiol | olefin | thione | alcohol |
| 32 | CH$_3$SH | 86.5 | 79.2 | 15.6 | 2.9 | 2.3 |
| 33 | H$_3$C\\CH—SH/H$_3$C | 84.5 | 90.5 | 7.1 | 1.8 | 0.6 |
| 34 | H$_3$C-(CH$_2$)$_{10}$-CH$_2$SH | 60.0 | 95.8 | 0.8 | 1.7 | 1.7 |

It is seen that comparable results are obtained with a primary and a secondary thiol. Under such conditions, the catalyst is very stable and the stability is independent from the nature of the chosen thiol partner.

The invention is not limited to the embodiments and examples described hereinabove. Many variants and modifications can be envisaged by those skilled in the art, without departing from the spirit and scope of the invention as defined in the appended claims.

What is claimed is:

1. A process for the preparation of a primary or secondary mercaptan from the corresponding thiocarbonyl compound selected from the group consisting of the thio-aldehyde and the thio-ketone, wherein the thiocarbonyl compound is heated in the presence of a primary or secondary mercaptan, and of a catalyst so as to cause a hydrogen exchange between the mercaptan and the thiocarbonyl compound, wherein said catalyst is constituted by at least one oxide of a metal selected from the groups II and III of the Periodic Table.

2. A process according to claim 1, wherein the preparation is carried out at a temperature comprised between 100° and 300° C.

3. A process according to claim 1, wherein the preparation is carried out at a temperature comprised between 100° and 300° C., the catalyst being activated by an alkaline base.

4. A process according to claim 1, wherein the formation of the thio-aldehyde or the thio-ketone is performed in situ simultaneously with the hydrogen exchange, the former being obtained by the action of the hydrogen sulphide on an aldehyde or ketone, in the presence of a mercaptan.

5. A process according to claim 4, wherein the aldehyde or ketone is alkyl, cycloalkyl, arylic or aryl-alkyl.

6. A process according to claim 4, wherein the molar ratio of the hydrogen sulphide to the aldehyde or the ketone is is at least 5.

7. A process according to claim 4, wherein the molar ratio of the hydrogen sulphide to the aldehyde or the ketone is comprised between 5 and 30.

8. A process according to claim 1, wherein the molar ratio of the mercaptan to the aldehyde or the ketone is at least 3.

9. A process according to claim 1, wherein the molar ratio of the mercaptan to the aldehyde or the ketone is comprised between 3 and 10.

10. A process according to claim 1, wherein the temperature is between 150° and 300° C., and the catalyst is alumina.

11. A process according to claim 10, wherein the catalyst is activated by an alkaline base.

12. A process according to claim 1, wherein the catalyst is magnesium oxide or a mixture of magnesium oxide and alumina.

13. A process according to claim 1, wherein the contact between the gaseous reaction medium and the catalyst is maintained for 1 to 16 seconds.

14. A process according to claim 1, wherein the pressure of the gaseous reaction medium is at least equal to atmospheric pressure.

15. A process according to claim 4 wherein the preparation is carried out at a temperature comprised between 150° and 300° C., the catalyst is alumina activated by 2-10 percent of a potassium containing base, the molar ratio of the hydrogen sulfide to the aldehyde or the ketone is at least 5 and the molar ratio of the mercaptan to the aldehyde or the ketone is at least 3.

* * * * *